(12) United States Patent
Maender et al.

(10) Patent No.: US 7,718,722 B2
(45) Date of Patent: May 18, 2010

(54) ALKYLTHIO- AND ARYL(HETEROYL)THIO-SUBSTITUTED P-PHENYLENEDIAMINES, THEIR MANUFACTURE AND THEIR USE IN RUBBER

(75) Inventors: Otto William Maender, John's Island, SC (US); Charles John Rostek, Chagrin Falls, OH (US); Alan Roy Katritzky, Gainesville, FL (US); Herman Howard Odens, Wilmington, DE (US); Michael Victor Voronkov, Cranbury, NJ (US)

(73) Assignee: Flexsys America L.P., Akron, OH (US)

( * ) Notice: Subject to any disclaimer, the term of this patent is extended or adjusted under 35 U.S.C. 154(b) by 403 days.

(21) Appl. No.: 10/441,808

(22) Filed: May 20, 2003

(65) Prior Publication Data
US 2004/0006162 A1    Jan. 8, 2004

Related U.S. Application Data

(63) Continuation-in-part of application No. 09/999,089, filed on Nov. 20, 2001, now abandoned.

(60) Provisional application No. 60/252,679, filed on Nov. 21, 2000.

(51) Int. Cl.
C08K 5/18       (2006.01)
C08K 5/375      (2006.01)
C08K 5/378      (2006.01)
C08L 9/00       (2006.01)
C07C 211/51     (2006.01)

(52) U.S. Cl. .................. 524/237; 524/236; 524/393; 524/392; 524/83; 524/84; 524/99; 524/100; 524/104; 524/106; 525/331.9; 525/333.1; 525/333.2; 525/332.9; 564/305; 568/38

(58) Field of Classification Search .................. 524/83, 524/392, 393, 95, 96, 236, 396, 237, 84; 525/333.1, 332.6, 347, 348, 349, 351; 564/305
See application file for complete search history.

(56) References Cited

U.S. PATENT DOCUMENTS

| | | | | |
|---|---|---|---|---|
| 2,991,271 | A |   | 7/1961 | Albert .................. 260/45.9 |
| 3,882,186 | A | * | 5/1975 | Cain et al. .................. 525/346 |
| 3,898,205 | A | * | 8/1975 | Hopper et al. .............. 525/348 |
| 4,137,310 | A | * | 1/1979 | Wang .......................... 514/107 |
| 4,377,634 | A |   | 3/1983 | Mifune et al. ............... 430/440 |
| 4,767,809 | A | * | 8/1988 | Wingrove .................... 524/255 |
| 4,851,419 | A | * | 7/1989 | Cox et al. .................... 514/338 |
| 5,113,019 | A |   | 5/1992 | Vottero et al. ................. 568/42 |
| 5,120,779 | A | * | 6/1992 | Cornell et al. .............. 524/100 |
| 5,414,131 | A |   | 5/1995 | Hert et al. ................... 564/440 |
| 5,542,952 | A | * | 8/1996 | Genet et al. ..................... 8/410 |
| 5,959,126 | A | * | 9/1999 | Lohr et al. ................... 552/301 |
| 6,025,508 | A | * | 2/2000 | Lodaya et al. ............... 552/301 |
| 6,114,554 | A | * | 9/2000 | Lodaya et al. ............... 552/301 |
| 2003/0028977 | A1 | * | 2/2003 | Lang ............................ 8/405 |

FOREIGN PATENT DOCUMENTS

| | | |
|---|---|---|
| DE | 1157030 | 11/1963 |
| EP | 0001604 | 5/1979 |
| EP | 0 481 333 A1 | 4/1992 |
| EP | 0 775 719 A2 | 5/1997 |
| WO | WO 96/22972 | 8/1996 |

OTHER PUBLICATIONS

Zincke, T.; Jorg, P. Berichte, 1911, 614-626.*
Snell et al., J. Am. Chem. Soc., 1938, 61, 450-453.*
JACS 61, pp. 450-453 (1938); The Reaction of Thiol Compounds with Quiones, Snell et al.
Rubber chemisty of N-substitiuted quinone imines and N,N'-disubstituted quinone diimines. Plastics and Rubber: Processing Sep. 1977, pp. 83-86, Gelling, et al.
Rubber Technology Hand book (1989) pp. 264-277. W. Hoffman.
Derwent Abstract No.: 94-148871/18 abstracting Swedish Patent No.: SU 1796618-A1.
Derwent Abstract No.: 89-159434/22 abstracting European Patent No.: EP 318394A.
Derwent Abstract No.: 96-362609/36 abstracting PCT No.: WO 96/22972-A1.
Derwent Abstract No.: 97-283087/26 abstracting European Patent No.: EP 77/5719-A2.
Derwent Abstract No.: 93-0966755/12 abstracting Japanese Patent No.: JP 05039257-A.
Derwent Abstract No.: 92-305008/37 abstracting Japanese Patent No.: JP 04211644-A.
Derwent Abstract No.: 92-305009/37 abstracting Japanese Patent No.: JP 04211646-A.
Derwent Abstract No.: 90-331964/44 abstracting Japanese Patent No.: JO 2239-247-A.
Derwent Abstract No.: 00-3507865 abstracting Japanese Patent No.: JP 57085366-A2.
Derwent Publication No. 33515B/18, Abstract of EP0001604.
T. Zincke, et al., "Uber 1,4-Amnothiophenol III", Berichte Der Deutschen Chemischen Gesellschaft, vol. 44, 1911, pp. 614-626, XP002220429, Verlag Chemie, Weinheim, DE Compounds VII, X.
J.D. Scribner, et al.: "Intramolecular Hydrogen Bonding in o-methylmercapto derivatives of N-methylaniline and N-Methyl—aminoazobenzene" Journal of Organic Chemistry, vol. 32, No. 7, (Jul. 1967), pp. 2348-2349, XP002220292, American Chemical Society, Washington, DC, US ISSN: 0022-3263, p. 2348.
International Search Report of International Application No. PCT/US01/45213.

* cited by examiner

*Primary Examiner*—David Wu
*Assistant Examiner*—Rip A. Lee
(74) *Attorney, Agent, or Firm*—Brinks Hofer Gilson & Lione

(57) ABSTRACT

A composition comprising alkylthio- or aryl(heteroyl)thio-substituted p-phenylenediamine, its method of preparation, and its use as an antidegradant in natural or synthetic rubber.

37 Claims, No Drawings

ALKYLTHIO- AND ARYL(HETEROYL)THIO-SUBSTITUTED P-PHENYLENEDIAMINES, THEIR MANUFACTURE AND THEIR USE IN RUBBER

CROSS REFERENCE TO RELATED APPLICATIONS

This application is a continuation-in-part of U.S. patent application Ser. No. 09/999,089, filed Nov. 20, 2001, now abandoned, that claims priority from Provisional Patent Application No. 60/252,679, filed Nov. 21, 2000, now abandoned, all the contents of which are incorporated herein by reference.

BACKGROUND OF THE INVENTION

1. Field of the Invention

The invention relates to alkylthio- and aryl(heteroyl)thio-substituted p-phenylenediamines, their manufacture and use as antidegradants in rubber compounds.

2. Discussion of the Prior Art

Vulcanizing rubber compositions by heating a sulfur-vulcanizable rubber composition with sulfur and/or a sulfur donor and a vulcanization accelerator has been known for many years. By this process vulcanizates having acceptable physical properties including tensile strength, resilience, and fatigue resistance can be obtained, but such vulcanizates tend not to have good aging properties.

Uncured as well as cured rubbers are prone to aging effects. The unsaturated groups in diene rubbers, e.g. styrene-butadiene rubber (SBR) or a blend of SBR with natural rubber, butadiene rubber or with both, make it possible to cure with sulfur, but at the same time they exhibit a sensitivity toward oxygen, ozone, and other reactive substances causing changes such as hardening of the vulcanizate. Unaged diene rubbers contain free double bonds that remain sensitive to the above reactive substances even after vulcanization. Higher temperatures make these effects even more noticeable.

Protective agents are used to protect the rubber vulcanizate against various forms of aging, fatigue, and ozone. For example, exposure of pneumatic tires to ozone leads to the formation of ozone cracks, in particular in the sidewalls of the tire. A well-known class of protective agents are N,N'-di-substituted, in particular N-alkyl-N'-phenyl-p-phenylenediamine derivatives. These N,N'-di-substituted p-phenylenediamine derivatives typically are also referred to as antidegradants, antiozonants or antioxidants. The reader is directed to Hofmann, *Rubber Technology Handbook*, Hanser Publishers, Munich 1989, pp. 264-277, in particular pp. 269-270. These antidegradants are commercially available inter alia under the trademark Santoflex® sold by Flexsys America L.P. In the rubber industry, the most frequently used antidegradant is N-(1,3-dimethylbutyl)-N'-phenyl-p-phenylenediamine or 6PPD.

Known 1,4-benzoquinone diimines (QDI's) can be classified under three major categories: I, II and III. Class I compounds contain no substituents attached to the benzoquinoid ring. Class II, the largest group, contains amino-substituents at the 2- and 5-positions of the benzoquinoid ring. Class III comprises all other p-benzoquinone diimines.

Many benzoquinone diimines (QDI's) were previously prepared by the oxidation of phenylenediamine derivatives with manganate, ferricyanate, iodine, silver ion, silver oxide, and lead tetraacetate (or "red lead").

Oxidation of N,N'-diphenyl-p-phenylenediamine with $Ag_2O$ gives N,N'-diphenyl-p-phenylenediimine. Oxidation of N-(1,3-dimethylbutyl)-N'-phenyl-1,4-phenylenediamine (6PPD) an effective antiozonant and antioxidant used in rubber industry, with $Ag_2O$ gives the corresponding QDI in 55% yield; similar conversion is achieved by photocatalytic oxidation using $Ru^3$. The QDI can be prepared by two consecutive photo cleavages of NO groups from the bis-nitroso derivative of N,N'-diphenyl-p-phenylenediamine.

N,N'-Diaryl-2,5-bis(arylamino)-p-benzoquinone diimines or azophenines, which belong to the second class of QDI's and are dye intermediates, have been synthesized by a wide variety of methods many of which involve the separation of resulting mixtures and afford low yields. Parent azophenine has been prepared by heating p-benzoquinonedianil with aniline. Substituted azophenines are also formed in 25-35% yields by oxidation of anilines on heating with 1,1,2,2-tetrachloroethane or hexachloroethane in the presence of copper bronze. The oxidation of aniline by 3- and 4-azidopyridine-1-oxides also gives azophenines. Peroxidase oxidation of 4-chloroaniline gives 2-amino-5-chloroanilinobenzoquinone di-4-chloroanil. Benzoquinone diimines are formed as side products in the decomposition of the corresponding nitroxide.

N,N'-Bis[phenylsulfonyl]-1,4-benzoquinone diimine is sulfanylamidated by sodium N-chlorobenzenesulfonamide to form 2,5-bis(phenylsulfonylamino)-N,N'-bis(phenylsulfonyl)-1,4-benzoquinone diimine. Similarly, amidation of N,N'-bis[phenylsulfonyl]-1,4-benzoquinone diimine with N-chloroamides gives the corresponding sulfonyl benzoquinone diimine derivatives in one step.

Few synthetic procedures are known for the preparation of representatives of class III of benzoquinone diimines. For example, many symmetrical and unsymmetrical N,N'-bis (arylthio)- and N,N'-bis(arylseleno)-quinone diimines have been prepared by treatment of N,N'-dichloroquinone diimines with thiols or selenols, respectively.

More recently, N,N'-dicyanoquinone diimine (DCNQI) salts have gained attention due to their high conductivity and ease of synthesis from benzoquinones and bis(trimethylsilyl) carbodiimide.

A synthetic route to poly(quinone diimines) via the treatment of anthraquinone (AQ) with aromatic diamines in the presence of $TiCl_4$ and 1,4-diazabicyclo[2.2.2]octane (Dabco) has been developed.

Employing the same model as above, some heterocyclic quinone arylimines have been prepared through Wittig addition of (N-aryl)triphenylarsinimines to the carbonyl functionality of heterocyclic benzoquinone derivatives. Polyaromatic quinone imines are readily formed by reactions of the corresponding quinones with triphenylarsine oxide and aryl isocyanates.

Most reactions of p-benzoquinone diimines fall into two broad types: reduction and addition. The reactivity of benzoquinone diimines (QDI) is dictated by a strong tendency to form a stable benzenoid structure. Therefore, they are very reactive towards nucleophilic addition and undergo reduction more readily than quinones. Most published reactions of QDI's relate to studies of the relatively stable diacyl and disulfonyl derivatives.

In the publication by Snell and Weissberger, *The Reaction of Thiol Compounds with Quinones*, JACS 61, 450(1938), the reactions between thiol compounds with benzoquinone and substituted benzoquinones were discussed. The article stated that two types of reaction may be expected: oxidation of the thiol to a disulfide with reduction of the quinone to the hydroquinone; and addition of the thiol to the quinone to obtain alkylthio substituted quinones and/or hydroquinones.

In Gelling and Knight, *Rubber chemistry of N-substituted quinone imines and N,N'-disubstituted quinone diimines*, Plastics and Rubber Processing September 1977, findings were discussed concerning two distinct reactions that occur between 2-mercaptobenzothiazole (MBT) and N-cyclohexyl-N'-phenylquinone diimine.

The major reaction involves 1,4-addition of the MBT across the diimine ring to yield the addition product. There is also an oxidation-reduction reaction to yield N-cyclohexyl-N'-phenyl-p-phenylenediamine and 2,2'-dithio-bis(benzothiazole).

SUMMARY OF THE INVENTION

In one embodiment, the present invention comprises a composition comprising alkylthio- or aryl(heteroyl)thio-substituted p-phenylenediamines having the formula:

Formula I:

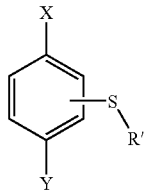

Where:

X and Y are the same and comprise NHR, where R is alkyl, cycloalkyl or aryl, or X and Y are different and selected from the group $NH_2$, or NHR (where R is alkyl, cycloalkyl or aryl); and R' is alkyl, cycloalkyl, aryl, alkyl 3-propionate, or a carbon based heterocycle containing at least one of S or N, or both S and N.

In a second embodiment, the present invention comprises a process for the manufacture of the above compositions comprising reacting a quinone diimine and a thiol in accordance with the following reaction equation:

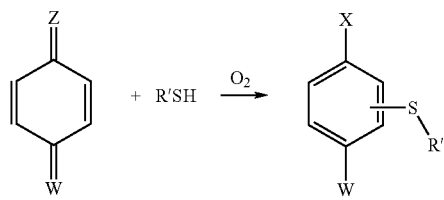

Where Z and W are the same and comprise NR or different and selected from the group NH, or NR with R and R' the same or different and selected from the groups alkyl, cycloalkyl or aryl and where X and Y are the same and comprise NHR or different and selected from the groups $NH_2$ or NHR.

In a third embodiment, the present invention comprises a composition comprising natural or synthetic rubber, or a blend thereof, and one or more antidegradants selected from the above Formula I.

Other embodiments of the invention encompass specific p-phenylenediamines, details concerning their manufacture, and relative amounts of reactants and natural or synthetic rubber compositions, all of which are hereinafter disclosed in the following discussion of each of the facets of the present invention.

DETAILED DESCRIPTION OF THE INVENTION

Quinonediimines have been described as primary intermediates in the action of p-phenylenediamines as antioxidants and antiozonants. Quinoid structures are highly reactive, undergoing addition reactions by means of either free radical or polar mechanisms. The formation of alkylthio- and 2,5-bis-amino-1,4-phenylenediamines may be accomplished by the addition of thiols and amines to N-(1,3-dimethylbutyl)-N'-phenyl-1,4-quinonediimine in the presence of air.

According to the present invention, it has been found that by adding appropriate amounts of the above alkylthio- or aryl(heteroyl)thio-substituted p-phenylenediamines of Formula I to a vulcanizable rubber composition comprising natural rubber or other rubbers, vulcanizates, from which, e.g., pneumatic tires can be made, having improved anti-aging, fatigue, and ozone resistance properties, can be obtained.

In this application, the abbreviation "phr" means the number of parts by weight per 100 parts by weight of rubber. In the case of a rubber blend, it is based on 100 parts by weight of total rubber.

Either natural rubber (NR), styrene-butadiene rubber (SBR) or a blend of NR and SBR or NR and SBR with one or more other rubbers can be used in the invention process, it being understood that for purposes of this invention the term "rubber" means an elastomer containing a hydrocarbon unit which is a polymer with some unsaturated chemical bonds. Typically, SBR, a blend of SBR with natural rubber (NR), a blend of SBR with polybutadiene rubber or butadiene rubber (BR), or a blend of SBR with NR and BR is used. The type of rubber or mixture of rubbers will have some effect on the precise amounts of antidegradant to be used.

Typically, the amount of antidegradant employed in the rubber composition of the present invention will be at least about 0.5 phr. The preferred upper limit is about 5.0 phr, most preferably 3.0 phr.

In a preferred embodiment, the composition of Formula I comprises a heteroylthio-substituted p-phenylenediamine wherein R' is a heterocyclic moiety selected from the group consisting of 2-pyrazines, 3-pyrimidines, 2,3,4-pyridines, 2-pyrimidines, 2-(4,6-dimethyl) pyrimidines and triazenes.

In another preferred embodiment, the above alkylthio- or aryl(heteroyl)thio-substituted p-phenylenediamine structure of Formula I may comprise a heteroylthio-substituted p-phenylenediamine wherein R' is a heterocyclic moiety selected from the group consisting of 2-pyrazines, 3-pyrimidines, 2-, 3-, 4-pyridines, 2-pyrimidines, 2-(4,6-dimethyl) pyrimidines and triazenes.

Where R' of Formula I connects the same or different p-phenylenadiamine moieties via a bridging group, this group is denoted by —(R"—Z—R''')—, where Z is O, NH, NR, S, —SS—, or —(CH$_2$)nCO(R''')OC(CH$_2$)n—, where n=1-3 and R" and R''' are selected from the group consisting of alkylene, arylene, pentaerithrityl and carbon based heterocyclic groups containing at least one of S or N, or both S and N. A highly preferred composition is a heteroylthio-substituted p-phenylenediamine wherein R' is a heterocyclic moiety selected from the group consisting of 1,3,5-triazinyl, 2,5-thiadiazolyl and 2,6-pyridyl.

In the above embodiment of the present invention for a process for the manufacture of alkylthio- or aryl(heteroyl) thio-substituted p-phenylenediamines, the preferred amount of R'SH employed in the reaction is from about 10% to about 90% of the stoichiometry required to make a 1:1 adduct, resulting in a reaction product comprising a blend of alkylthio- or aryl(heteroyl)thio-substituted p-phenylenediamines and unreacted quinone diimine.

The most preferred embodiment of the above Formula I of the present invention for a process for the manufacture of alkylthio- or aryl(heteroyl)thio-substituted p-phenylenediamines is in accordance with the following reaction Equation 1 (R' is as defined in Formula I):

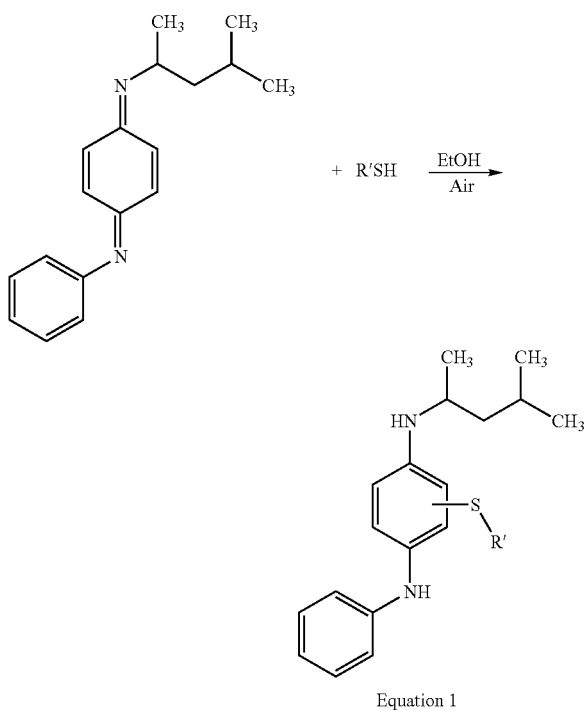

Equation 1

Preferred reaction conditions for the addition reaction of the present invention comprise stirring the reactants dissolved in an appropriate solvent, such as ethanol, for as little as about 2 hours under a constant stream of air from about 20° C. to about 25° C. Surprisingly, the oxidative conditions lead to simple and selective addition of the mercaptan to the quinoidal ring without generating disulfide by-products which can occur under oxidative conditions described in the prior art.

The composition of the present invention may comprise natural or synthetic rubber or a blend thereof and one or more antidegradants selected from the composition of Formula I. A preferred rubber is polyisoprene. The most preferred antidegradent is the reaction product of Equation I.

The natural or synthetic rubber or blend thereof may comprise a mixture of two or more antidegradants selected from the antidegradants of Formula I or one or more antidegradants selected from the antidegradants of Formula I in combination with a non-thio antidegradant. Preferred non-thio-substituted antidegradants are selected from the group consisting of phenylenediamines, dihydroquinolines and phenolics, or a blend thereof.

It is preferred that the alkyl, cycloalkyl, aryl, arylene and alkylene groups of the composition of the present invention have from 2 to about 18 carbon atoms and most preferably 2 to about 12 carbon atoms.

A typical rubber composition in accordance with the present invention comprises a rubber, about 0.1 to about 5 phr of sulfur, about 0.5 to about 2 phr of a vulcanization accelerator, preferably a sulfenamide accelerator, about 0.1 to about 5 phr (preferably about 2 to about 3 phr) of the antidegradant of the invention and a $C_{12}$-$C_{20}$ fatty acid such as stearic acid. Metal oxides such as zinc oxide typically are added to rubber compositions.

The rubber composition of the present invention typically also comprises a reinforcing filler in a conventional amount. Any carbon black or combination of carbon black with any silica may be used.

Conventional rubber additives may also be incorporated in the rubber composition according to the present invention. Examples include antireversion agents, processing oils, tackifiers, waxes, phenolic antioxidants, pigments, e.g. titanium dioxide, resins, plasticizers, and factices. These conventional rubber additives may be added in amounts known to the person skilled in the art of rubber compounding. The reader is also referred to the Examples described below.

Conventional rubber additives may also be included in the sulfur-vulcanizable rubber composition in accordance with the present invention. Examples include reinforcing agents such as carbon black, silica, clay, whiting and other mineral fillers, processing oils, tackifiers, waxes, phenolic antioxidants, phenylenediamine antidegradants, antiozonants, pigments, e.g. titanium dioxide, resins, plasticizers, factices, and vulcanization activators, such as stearic acid and zinc oxide. These conventional rubber additives may be added in amounts known to the person skilled in the art of rubber compounding. The reader is also referred to the examples that are described below.

For further details on these typical rubber additives and vulcanization inhibitors, see W. Hofmann, *Rubber Technology Handbook*, Hanser Publishers, Munich 1989.

Finally, in specific applications it may also be desirable to include steel-cord adhesion promoters such as cobalt salts and bis-thiosulfates in conventional, known quantities.

The composition of the present invention is useful in the manufacture of many articles, including pneumatic tires, e.g., for passenger cars and trucks, and industrial rubber goods, which comprise the rubber vulcanizate obtained by the method of the invention.

The invention is illustrated by the following examples.

EXAMPLES 1-15

Each of these examples involved preparation of an N'-(1, 3-dimethylbutyl)-2-(sulfanyl-substituted)-N'-phenyl-1,4-benzenediamines by reacting N'-(1,3-dimethylbutyl)-N'-phenyl-p-quinone diimine with a mercapto derivative as summarized in Table 1. In each example, the p-quinone diimine (0.80 g, 3.0 mmol) was dissolved in ethanol (25 mL) and treated with the mercapto derivative (0.33 mL, 3.0 mmol) under a constant gentle stream of air. The dark reaction mixture was further stirred for as little as 2 hours and as long as 20 hours over a 20-25 C. temperature range. The solvent was then evaporated and the dark brown slurry was purified by silica gel column chromatography to give the corresponding p-phenylenediamine.

The oxidation induction times (OIT) of each mercapto derivative of examples 1-15 was obtained, thus indicatiing their respective capacities as antioxidants. In the OIT procedure, a sample of 0.5 wt. % antioxidant in a polymer[1] is used for DSC oxidation induction time analysis. The sample is run on a TA Instruments 2910 differential scanning calorimeter equipped with nitrogen delivery at 30 ml/min and 100% oxygen delivery at 70 ml/min. An isothermal program is used at 160° C. under oxygen until an oxidation exotherm is detected[2]. The sample is first equilibrated at 160° C. under nitrogen. Oxygen is then turned on when the isothermal step of the program starts. The oxidation induction time is measured from the point when oxygen is turned on to the onset of the oxidation exotherm.

[1] cis Polyisoprene made from synthetic rubber Average Mw ca. 40,000 (GPC) from Aldrich 43-126-5.
[2] The isothermal temperature can be adjusted for an antioxidant/polymer system to give an exotherm which occurs between about 15 min. to an hour.

Oxidation induction times were determined in polyisoprene at 160° C. and were also determined for N-(1,3-dimethylbutyl)-N'-phenyl-p-phenylene diamine which exhibited an average OIT of 13.5 minutes under the same conditions as the products of Examples 1-15 (see Table 1).

Superior antioxidant capacity is thus shown by the compounds of the present invention as compared to N-1,3-dimethylbutyl-N'-phenyl-p-phenylenediamine. From the OIT data of Table 1, it is observed that the use of the antidegradant of the present invention in polyisoprene in almost every instance is superior to that of N-(1,3-dimethylbutyl)-N'-phenyl-p-phenylene diamine.

The OIT of each mercapto derivative of Examples 1-15 is also shown in Table 1.

TABLE 1

Examples of Thio-substituted-p-phenylenediamines and Their Respective Oxidation Induction Times (OIT)[a]

| Example No. | Mercapto Derivative | OIT Minutes |
|---|---|---|
| 1 | Methyl 3-mercaptopropionate | 88.5 |
| 2 | Cyclohexyl mercaptan | 70.1 |
| 3 | Dodecyl mercaptan | 150.4 |
| 4 | Isopropyl mercaptan | 34.3 |
| 5 | n-Butyl mercaptan | 55.7 |
| 6 | t-Butyl mercaptan | 24.4 |
| 7 | Benzyl mercaptan | 44.5 |
| 8 | 2-Chlorobenzyl mercaptan | 61.7 |
| 9 | 1,5-Dimercaptoethyl ether | 121.0 |
| 10 | 2-Mercaptopyrimidine | 23.0 |
| 11 | 4,6-Dimethyl-2-mercaptopyrimidine | 6.8 |
| 12 | 2-Mercaptotoluimidazole | 31.2 |
| 13 | Phenyl mercaptan | 60.4 |
| 14 | 2-Carboxyphenyl mercaptan | 16.1 |
| 15 | 3-Hydroxy-2-mercaptopyridine | 89.0 |

EXAMPLE 16

Each of the thio-substituted-p-phenylenediamines of Examples 1-15 were subjected to an elemental analysis for nitrogen for determination that the desired addition reaction occured. The analyses for nitrogen is carried out by weighing the sample to be analyzed and subjecting it to quantitative oxidation in a stream of helium and oxygen at temperatures in excess of 1,000 degrees centigrade. After complete combustion, the gasses are passed through a reductor which is packed with copper wire or mesh heated to 650 degrees centigrade. The reductor, by eliminating the excess oxygen, leaves the three combustion gasses (nitrogen, carbon dioxide, and water) ready for injection into the gas chromatograph, and can be considered the interface between the combustion section and the measurement (gas chromatography) section. The gas chromatography section separates the individual components of the gas stream so that they can be individually measured by the detection system. The chromatographic data are digitized, integrated, and mathematically processed to give the elemental composition of the sample.

Table 2 itemizes the yields, physical nature and analyses for nitrogen of the thio-substituted-p-phenylenediamines of Examples 1-15. The nitrogen found as well as the theoretical nitrogen for the structure in question is given. The difference between the two is within expected norms.

TABLE 2

| No. | Mercapto Derivative | Yield % | State - m.p. ° C. | N, Found (Theory) |
|---|---|---|---|---|
| 1 | Methyl 3-mercaptopropionate | 90 | Yellow oil | 7.53, (7.25) |
| 2 | Cyclohexyl mercaptan | 81 | Yellow oil | 7.22, (7.32) |
| 3 | Dodecyl mercaptan | 93 | Yellow oil | 6.20, (5.98) |
| 4 | Isopropyl mercaptan | 74 | Orange oil | 8.50, (8.18) |
| 5 | n-Butyl mercaptan | 76 | Orange oil | 7.76 (7.86) |
| 6 | t-Butyl mercaptan | 85 | Orange oil | 7.72 (7.86) |
| 7 | Benzyl mercaptan | 89 | Brown oil | 7.46, (7.17) |
| 8 | 2-Chlorobenzyl mercaptan | 88 | Brown oil | 6.74, (6.59) |
| 9 | 1,5-Dimercaptoethyl ether | 93 | Brown tar | |
| 10 | 2-Mercaptopyrimidine | 71 | Beige solid 103-106 | 14.37 (14.81) |
| 11 | 4,6-Dimethyl-2-mercaptopyrimidine | 87 | Beige solid 88-91 | 13.83 (13.78) |
| 12 | 2-Mercaptotoluimidazole | 50 | Yellow solid 73-75 | |
| 13 | Phenyl mercaptan | 75 | Amber oil | |
| 14 | 2-Carboxyphenyl mercaptan | 80 | Yellow solid 119-121 | 6.66, (6.64) |
| 15 | 3-Hydroxy-2-mercaptopyridine | 65 | Black oil | |

EXAMPLE 17

A masterbatch of rubber, carbon black, lubricant/softener (aromatic oil), and antidegradant was made in an internal mixer. The sulfur, accelerator, and antidegradant were mixed on a two-roll mill at approximately 70-80° C.

Cure characteristics were determined using a Monsanto rheometer ODR 2000E (range 0-100 dNm/arc 1.0°, ASTM D2084-93). Delta torque (Delta S) is the maximum torque ($M_H$) minus the minimum torque ($M_L$). Scorch time or scorch safety ($t_S2$) is the time at 2% increase of the minimum torque ($M_L$). Optimum vulcanization or cure time ($t_{90}$+5 min.) is the time required to achieve maximum torque ($M_H$).

Rubber compounds were vulcanized by compression molding at 150° C. for $t_{90}$. After cooling the vulcanized rubber sheets for 24 h, test pieces were cut and analyzed.

Tensile measurements were carried out using a Alpha Technologies T-10 tensile tester (ASTM D412-C dumbbell).

The tensile stress-strain properties were determined in accordance with ASTM D412, the tear strength was determined in accordance with ASTM D624-91, and the fatigue to failure (0-100% extension) in accordance with ASTM 4482/85.

The ozone resistance was tested by comparing the antiozonant capacity of experimental compounds in rubber to that of commercial antidegradants, e.g. Santoflex 6PPD, and unprotected rubber.

Stress-strain sheets comprising a rubber formulation that can contain an antidegradant composition are cured in a mold for a time equivalent to that required to achieve a rheometer torque optimum at 150 C. Ozone test specimens are cut from these uniform stress-strain sheets, using a T-50 die (ASTM D2137 with dimensions of 2.54 mm width by 50.8 mm length with a 6.35 mm square at each end to fasten the rubber specimen for testing). These labeled samples are stretched in a standard tensile test machine to obtain the force required to stretch 100% (F(subscript: o)). The test specimens are then exposed to an ozone concentration of 25 pphm at 40° C. in an ozone chamber for periods of 16 hours.

During ozone exposure, the specimens are stretched in racks to a constant 25% extension (static) and are also inserted between two movable disks that allow flexing (extension of 25%) of the rubber specimen under intermittent and continuous (dynamic) cycles. Thus, 3 specimens of each rubber compound are tested concurrently; one static, one intermittent, and one dynamic. Both the dynamic and intermittent disks flex the samples 96 times per minute. Samples are flexed by the intermittent disks for 18 minutes every 2 hours while dynamic flexing proceeds continuously. After 16 hours of ozone exposure the specimens are again tested on the tensile machine to obtain force after aging (F(subscript: t)). The retention value, F (subscript: t)/F(subscript: 0) is calculated and the process of exposure and tensile testing is repeated until the retention value falls below 70% for all the specimens or the specimen breaks due to catastrophic crack formation. The hours to failure or 70% retention of initial force are determined via a regression analysis program and serve as a measure of ozone resistance. Unaged and aged (hot air at 100 C. for 24 hrs.) T-50 specimens are tested in this manner to measure persistence of the antiozonant in the vulcanizate.

The rubber test pieces were aged under one of the following conditions to simulate the service life of rubber during use, for example, as a tire. The test specimens were aged in an air circulation oven for 24, 48 and 72 hours at 100° C.

The masterbatches employed in the compositions were compounded as shown in Tables 3 and 6. The various Stocks comprised the compositions as shown in Tables 4 and 7. The respective kinetic and physical properties are shown in Tables 5 and 8.

For the purpose of comparison, the known antidegradants, Santoflex®6PPD[3], Flectol®TMQ[4], and Wingstay®100[5] were employed to formulate the various control compounds "C".

The terms "Example #1" and "Example #3" as used in the following discussion are intended to mean the products of the above Example #1 and Example #3 in Table 1, respectively.

TABLE 3

SBR Masterbatch

| Ingredients | phr |
|---|---|
| SBR 1500 | 100 |
| N-330 Carbon Black | 50 |
| Flexon 580[6] | 10 |
| Zinc Oxide | 4 |
| Stearic Acid | 2 |
| | 166 |

TABLE 4

SBR Stock Compositions

| Stock Number | 1 | 2C | 3C | 4C | 5 | 6 |
|---|---|---|---|---|---|---|
| SBR Masterbatch | 166.0 | 166.0 | 166.0 | 166.0 | 166.0 | 166.0 |
| Sulfur | 2.0 | 2.0 | 2.0 | 2.0 | 2.0 | 2.0 |
| Santocure ® CBS[7] | 1.2 | 1.2 | 1.2 | 1.2 | 1.2 | 1.2 |
| Santoflex ® 6PPD | — | 2.0 | — | — | — | — |
| Flectol ® TMQ | — | — | 2.0 | — | — | — |
| Wingstay ® 100 | — | — | — | 2.0 | — | — |
| Example #1 | — | — | — | — | 2.0 | — |
| Example #3 | — | — | — | — | — | 2.0 |

[3]N-(1,3-Dimethylbutyl)-N-p-phenylenediamine
[4]2,2,4-Trimethyl-1,2-dihydroquinoline
[5]phenyl-orthotolyl-p-phenylenediamine
[6]Naphthenic petroleum oil, ASTM type 103
[7]N-Cyclohexyl-2-benzothiazolesulfenamide

TABLE 5

Kinetic and Physical properties in SBR (refer to Table 5 for Stock compositions)

| Stock Number | 1 | 2C | 3C | 4C | 5 | 6 |
|---|---|---|---|---|---|---|
| Mooney Scorch @ 135 C. | | | | | | |
| Min. Viscosity | 36.1 | 32.7 | 34.4 | 33.6 | 33.3 | 33.3 |
| t 5, Minutes | 29.1 | 24.3 | 29.8 | 25.0 | 27.3 | 28.8 |
| t 35, Minutes | 38.8 | 30.8 | 38.4 | 34.4 | 36.2 | 39.3 |
| Rheometer @ 150 C. | | | | | | |
| Max. Torque, dNm | 43.0 | 41.1 | 40.5 | 41.8 | 41.3 | 39.7 |
| Min. Torque, dNm | 6.0 | 5.5 | 5.7 | 5.7 | 5.8 | 5.7 |
| t 2, Minutes | 12.2 | 11.0 | 12.5 | 11.1 | 11.7 | 12.6 |
| t 90, Minutes | 34.7 | 27.8 | 31.6 | 29.8 | 31.1 | 32.7 |
| t 90 - t 2, Minutes | 22.5 | 16.8 | 19.1 | 18.7 | 19.4 | 20.1 |
| Stress-Strain Data (Unaged) Cured (t 90 + 5) Min. @ 150 C. | | | | | | |
| Tensile, MPa | 21.4 | 24.2 | 23.8 | 24.5 | 21.9 | 23.3 |
| 100% Modulus, MPa | 2.4 | 2.2 | 2.2 | 2.3 | 2.2 | 2.1 |
| 300% Modulus, MPa | 12.3 | 11.4 | 11.2 | 11.8 | 11.5 | 10.9 |
| % Elongation | 465 | 557 | 548 | 546 | 496 | 553 |
| Shore "A" Hardness | 61 | 61 | 61 | 61 | 61 | 60 |
| Stress-Strain Data (Aged) Hot Air Aged 48 hrs. @ 100 C. | | | | | | |
| Tensile, MPa | 17.1 | 18.7 | 19.8 | 17.7 | 18.2 | 18.1 |
| 100% Modulus, MPa | 4.8 | 4.4 | 4.8 | 4.5 | 4.5 | 4.5 |
| 200% Modulus, MPa | 12.9 | 11.8 | 12.7 | 12.0 | 12.1 | 12.2 |
| % Elongation | 249 | 300 | 295 | 281 | 282 | 278 |
| Shore "A" Hardness | 64 | 68 | 65 | 70 | 69 | 67 |
| T50 Ozone Test (Unaged) | | | | | | |
| Static (Hrs to 70% Mod. Ret.) | 17 | 214 | 15 | 46 | 30 | 22 |
| Intermittent (Hrs 70% Mod. Ret.) | 35 | 162 | 41 | 75 | 60 | 50 |
| Dynamic (Hrs to 70% Mod. Ret.) | 25 | 116 | 41 | 93 | 72 | 53 |
| T50 Ozone Test (Aged) 24 Hrs. @ 100 C. | | | | | | |
| Static (Hrs to 70% Mod. Ret.) | 17 | 32 | 18 | 32 | 27 | 24 |
| Intermittent (Hrs 70% Mod. Ret.) | 24 | 61 | 31 | 62 | 42 | 44 |
| Dynamic (Hrs to 70% Mod. Ret.) | 31 | 64 | 48 | 87 | 67 | 53 |

TABLE 6

NR Masterbatch

| Ingredients | phr |
|---|---|
| SMR-CV 60[8] | 100 |
| N-330 Carbon Black | 50 |
| Flexon 580 | 5 |
| Zinc Oxide | 5 |
| Stearic Acid | 2 |
| | 162 |

[8]Viscosity-stabilized (Mooney viscosity level 60), high quality grade of natural rubber.

TABLE 7

NR Stock Compositions

| Stock Number | 1 | 2C | 3C | 4C | 5 | 6 |
|---|---|---|---|---|---|---|
| SBR Masterbatch | 162.0 | 162.0 | 162.0 | 162.0 | 162.0 | 162.0 |
| Sulfur | 2.0 | 2.0 | 2.0 | 2.0 | 2.0 | 2.0 |

TABLE 7-continued

NR Stock Compositions

| Stock Number | 1 | 2C | 3C | 4C | 5 | 6 |
|---|---|---|---|---|---|---|
| Santocure ® CBS | 0.8 | 0.8 | 0.8 | 0.8 | 0.8 | 0.8 |
| Santoflex ® 6PPD | — | 2.0 | — | — | — | — |
| Flectol ® TMQ | — | — | 2.0 | — | — | — |
| Wingstay ® 100 | — | — | — | 2.0 | — | — |
| Example #1 | — | — | — | — | 2.0 | — |
| Example #3 | — | — | — | — | — | 2.0 |

TABLE 8

Kinetic and Physical properties in NR (refer to Table 7 for Stock compositions)

| Stock Number | 1 | 2C | 3C | 4C | 5 | 6 |
|---|---|---|---|---|---|---|
| Mooney Scorch @ 135 C. | | | | | | |
| Min. Viscosity | 16.3 | 14.9 | 14.9 | 15.3 | 15.2 | 14.5 |
| t 5, Minutes | 14.2 | 13.5 | 14.6 | 13.1 | 13.5 | 15.0 |
| t 35, Minutes | 15.7 | 15.1 | 16.3 | 14.8 | 15.3 | 16.9 |
| Rheometer @ 150 C. | | | | | | |
| Max. Torque, dNm | 33.9 | 33.3 | 32.8 | 34.2 | 33.0 | 32.1 |
| Min. Torque, dNm | 2.4 | 2.3 | 2.2 | 2.4 | 2.3 | 2.1 |
| t 2, Minutes | 5.9 | 5.8 | 6.0 | 5.7 | 5.6 | 6.3 |
| t 90, Minutes | 11.4 | 11.1 | 11.2 | 10.9 | 11.0 | 11.8 |
| t 90 - t 2, Minutes | 5.5 | 5.3 | 5.2 | 5.2 | 5.4 | 5.5 |
| % Reversion | 13.9 | 17.2 | 16.5 | 18.0 | 17.0 | 18.3 |
| Stress-Strain Data (Unaged) Cured (t 90 + 5) Min. @ 150 C. | | | | | | |
| Tensile, MPa | 26.6 | 26.2 | 27.2 | 27.4 | 26.6 | 25.3 |
| 100% Modulus, MPa | 2.3 | 2.5 | 2.6 | 2.6 | 2.5 | 2.5 |
| 300% Modulus, MPa | 12.4 | 11.6 | 12.4 | 12.3 | 12.0 | 11.8 |
| % Elongation | 541 | 567 | 565 | 570 | 560 | 548 |
| Shore "A" Hardness | 61 | 59 | 60 | 61 | 59 | 58 |
| Stress-Strain Data (Aged) Hot Air Aged 72 hrs. @ 100 C. | | | | | | |
| Tensile, MPa | 8.7 | 19.9 | 21.6 | 17.0 | 20.0 | 18.5 |
| 100% Modulus, MPa | 2.8 | 4.2 | 4.4 | 4.4 | 4.0 | 4.0 |
| 300% Modulus, MPa | 0.0 | 16.2 | 17.1 | 16.3 | 15.6 | 15.5 |
| % Elongation | 244 | 370 | 383 | 314 | 390 | 361 |
| Shore "A" Hardness | 58 | 64 | 65 | 68 | 66 | 61 |
| Fatigue D4482-85 (Unaged) | | | | | | |
| Kilocycles to Failure (#8 Cam) | 51 | 293 | 125 | 212 | 99 | 72 |
| Fatigue (Aged 7 days @ 70 C.) | | | | | | |
| Kilocycles to Failure (#8 Cam) | 43 | 130 | 86 | 136 | 134 | 71 |
| Die C Tear (ASTM D624-91) 21 C. | | | | | | |
| Peak Stress, N/mm | 99.3 | 100.4 | 108.8 | 115.2 | 113.0 | 102.1 |
| Strain, % | 739 | 778 | 825 | 858 | 854 | 808 |
| Die C Tear (ASTM D624-91) 100 C. | | | | | | |
| Peak Stress, N/mm | 64.4 | 60.4 | 62.0 | 65.1 | 67.0 | 66.6 |
| Strain, % | 830 | 738 | 799 | 795 | 882 | 903 |
| T50 Ozone Test (Unaged) | | | | | | |
| Static (Hrs to 70% Mod. Ret.) | 20 | 65 | 19 | 48 | 46 | 42 |
| Intermittent (Hrs 70% Mod. Ret.) | 26 | 90 | 35 | 62 | 59 | 48 |
| Dynamic (Hrs to 70% Mod. Ret.) | 15 | 77 | 32 | 70 | 55 | 49 |
| T50 Ozone Test (Aged) 24 Hrs. @ 100 C. | | | | | | |
| Static (Hrs to 70% Mod. Ret.) | 20 | 31 | 24 | 44 | 46 | 40 |
| Intermittent (Hrs 70% Mod. Ret.) | 21 | 28 | 22 | 53 | 53 | 48 |
| Dynamic (Hrs to 70% Mod. Ret.) | 16 | 26 | 27 | 50 | 52 | 37 |

With reference to the SBR compositions, Table 4 Examples #1 and #3 were compared to Santoflex®6PPD, Flectol®TMQ, and Wingstay®100 on an equal weight basis. The higher molecular weight of Examples #1 and #3 means that, compared to the control Stocks (2-4C), there are less molar equivalents of antidegradant available to protect the rubber against deterioration. Despite this handicap, Examples #1 and #3 show competitive oxidative capacity after air aging for 48 hrs. at 100 C. (see Table 4). Surprisingly, Examples #1 and #3 exhibit a persistent antiozonant activity, particularly after aging under demanding dynamic conditions as shown in Stocks 5 and 6. While initial antiozonant activity by Examples #1 and #3 is moderate, it is maintained after aging. The comparison of unaged to aged dynamic ozone performance suggests that the higher molecular weight Examples #1 and #3 diffuse to the surface of rubber more slowly than 6PPD, but at a rate sufficient to promote longer-term protection against ozone attack.

The NR formulation and compositions evaluated are shown in Tables 6 and 7. Again, the comparison of Examples #1 and #3 to Santoflex®6PPD, Flectol®TMQ, and Wingstay®100 is made on an equal weight basis. As an indication of antioxidant capacity in compounded NR, Example #1 (Stock 5) shows the best retention of elongation, 70%, after aging and Example #3 (Stock 6) is competitive with the control stocks, 2C and 4C, in retaining elongation (see Table 8). Also in Table 8, Stocks 5 and 6 show good fatigue and tear strength properties, indicating a better preservation of the polysulfide crosslink network. This crosslink stabilization is further supported by better hot tear strength (100 C.) and elongation (strain, %) exhibited by both Examples #1 and #3 in Stocks 5 and 6, respectively.

Moreover, Examples #1 and #3 also show good retention of modulus during aged ozone testing with a clear advantage in aged antiozonant activity over Santoflex®6PPD in NR; compare the T50 Ozone test results of Stocks 5 and 6 to Stock 2 in Table 7.

Surprisingly, in both SBR and NR, Examples #1 and #3 show broad antidegradant activity that favors long-term protection of vulcanizates that may be attributed to molecular size, molecular shape, and a dual mode of action, e.g. chain-stopper and peroxide decomposition, in rubber.

The invention claimed is:

1. A composition comprising an alkylthio-, arylthio-, or heteroylthio-substituted p-phenylenediamine compound having the formula:

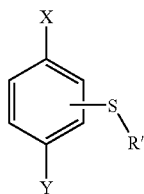

where:
X and Y each comprise NHR where R is one selected from the group of alkyl, cycloalkyl, or aryl when X and Y are the same, and R is one selected from the group of hydrogen, alkyl, cycloalkyl, or aryl when X and Y are different; and R' is one selected from the group of alkyl, cycloalkyl, aryl, 2-chlorobenzyl, 2-carboxyphenyl, benzyl, mercaptoethyl ether, alkyl 3-propionate, and a heterocyclic moiety, wherein the heterocyclic moiety is one selected from the group consisting of: 2-pyrazines, 3-pyrimidines, 2-pyridines, 3-pyridines, 4-pyridines, 2-pyrimidines, 2-(4,6-dimethyl)pyrimidines, 1,3,5-triazinyl, 2,6-pyridyl, 2,5-thiadiazolyl, 2-toluimidazole, 3-hydroxy-2-mercaptopyridine, and triazenes;

wherein when R' is alkyl, then R is cycloalkyl or aryl for at least one of X or Y;

wherein when X is $NH_2$ and Y is NHR with R being aryl, and R' is alkyl, then R' is a $C_2$-$C_{18}$ alkyl.

2. The composition of claim 1 comprising a heteroylthio-substituted p-phenylenediamine compound wherein R' is selected from the group consisting of 2-pyrazines, 3-pyrimidines, 2-pyridines, 3-pyridines, 4-pyridines, 2-pyrimidines, 2-(4,6-dimethyl)pyrimidines, 2,5-thiadiazole, 2-toluimidazole, and triazenes.

3. The composition of claim 1 wherein two p-phenylenediamine compounds are connected through its R' moiety via a bridging group denoted by —(R"—Z—R"')—, where Z is O, NH, NR, S, —SS—, or —$(CH_2)_n$CO(R''')OC$(CH_2)_n$—, with n=1-3 and R" and R''' selected as one from the group consisting of alkene, arylene, pentaerithrityl and carbon based heterocyclic groups containing at least one of S or N.

4. The composition of claim 1 comprising a heteroylthio-substituted p-phenylenediamine wherein R' is a heterocyclic moiety selected as one from the group consisting of 1,3,5-triazinyl, 2,5-thiadiazolyl and 2,6-pyridyl.

5. The composition of claim 1 wherein X is an alkyl amino group and Y is an aryl amino group.

6. The composition of claim 5 wherein R' is an alkyl group having from 2 to about 18 carbon atoms.

7. The composition of claim 5 wherein R' is selected as one from the group consisting of 1,3,5-triazinyl, 2,5-thiadiazolyl, and 2,6-pyridyl.

8. The composition of claim 1, wherein the p-phenylenediamine compound is a N'-(1,3-dimethylbutyl)-2-(sulfanyl-substituted) p-phenylenediamine.

9. The composition of claim 1, wherein the compound is one selected from the group consisting of N-(1,3-dimethylbutyl)-2-(methyl-3-mercaptopropionate)-N'-phenyl-1,4-benzenediamine; N-(1,3-dimethylbutyl)-2-(cyclohexyl mercaptan)-N'-phenyl-1,4-benzenediamine; N-(1,3-dimethylbutyl)-2-(isopropyl mercaptan)-N'-phenyl-1,4-benzenediamine; N-(1,3-dimethylbutyl)-2-(n-butyl mercaptan)-N'-phenyl-1,4-benzenediamine; N-(1,3-dimethylbutyl)-2-(t-butyl mercaptan)-N'-phenyl-1,4-benzenediamine; N-(1,3-dimethylbutyl)-2-(benzyl mercaptan)-N'-phenyl-1,4-benzenediamine; N-(1,3-dimethylbutyl)-2-(2-chlorobenzyl mercaptan)-N'-phenyl-1,4-benzenediamine; N-(1,3-dimethylbutyl)-2-(2-mercaptopyrimidine)-N'-phenyl-1,4-benzenediamine; N-(1,3-dimethylbutyl)-2-(1,5-dimercaptoethyl ether)-N'-phenyl-1,4-benzenediamine; N-(1,3-dimethylbutyl)-2-(4,6-dimethyl-2-mercaptopyrimidine)-N'-phenyl-1,4-benzenediamine; N-(1,3-dimethylbutyl)-2-(2-mercaptotoluimidazole)-N'-phenyl-1,4-benzenediamine; N-(1,3-dimethylbutyl)-2-(phenyl mercaptan)-N'-phenyl-1,4-benzenediamine; N-(1,3-dimethylbutyl)-2-(2-carboxylphenyl mercaptan)-N'-phenyl-1,4-benzenediamine; and N-(1,3-dimethylbutyl)-2-(3-hydroxy-2-mercaptopyridine)-N'-phenyl-1,4-benzenediamine.

10. A composition having the formula:

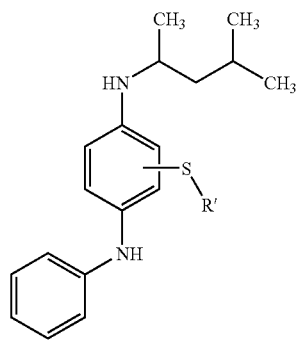

where R' is one selected from the group of alkyl, cycloalkyl, aryl, 2-chlorobenzyl, benzyl, 2-carboxyphenyl, mercaptoethylether, alkyl 3-propionate, and a heterocyclic moiety selected as one from the group consisting of: 2-pyrazines, 3-pyrimidines, 2-pyridines, 3-pyridines, 4-pyridines, 2-pyrimidines, 2-(4,6-dimethyl)pyrimidines, 1,3,5-triazinyl, 2,6-pyridyl, 2,5-thiadiazolyl, 2-toluimidazole, 3-hydroxy-2-mercaptopyridine, and triazenes.

11. The composition of claim 10, wherein —SR' is selected from the group consisting of methyl-3-mercaptopropionate, cyclohexyl mercaptan, dodecyl mercaptan, isopropyl mercaptan, n-butyl mercaptan, t-butyl mercaptan, benzyl mercaptan, 2-chlorobenzyl mercaptan, 1,5-dimercaptoethyl ether, 2-mercaptopyrimidine, 4,6-dimethyl-2-mercaptopyrimidine, 2-mercaptotoluimidazole, phenyl mercaptan, 2-carboxylphenyl mercaptan, and 3-hydroxy-2-mercaptopyridine.

12. An article of manufacture comprising a natural or synthetic rubber or blend thereof and one or more compounds having the formula:

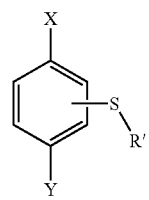

where:
X and Y each comprise NHR where R is one selected from the group of hydrogen, alkyl, cycloalkyl or aryl with R being aryl in at least one of X or Y; and R' is one selected from the group of alkyl, cycloalkyl, aryl, or alkyl 3-propionate, and a heterocyclic moiety selected as one from the group consisting of 2-pyrazines, 3-pyrimidines, 2-pyridines, 3-pyridines, 4-pyridines, 2-pyrimidines, 2-(4,6-dimethyl)pyrimidines, 1,3,5-triazinyl, 2,6-pyridyl, 2,5-thiadiazolyl, 2-toluimidazole, 3-hydroxy-2-mercaptopyridine, and triazenes.

13. A process for the manufacture of alkylthio- or heteroylthio-substituted p-phenylenediamine compounds, the process comprising reacting a quinone diimine and a thiol in accordance with the following reaction equation:

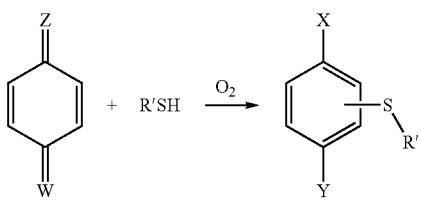

where

Z and W are independently selected from NH or NR;

X and Y are independently selected from $NH_2$ and NHR;

R is one selected from the group of alkyl, cycloalkyl or aryl; and

R' is one selected from the group of alkyl, cycloalkyl, aryl, 2-chlorobenzyl, 2-carboxyphenyl, benzyl, mercaptoethyl ether, alkyl 3-propionate, a carbon-based heterocycle containing at least one of S or N, a hydroxyl-substituted carbon-based heterocycle containing at least one of S or N, and an alkyl-substituted carbon-based heterocycle containing at least one of S or N.

14. The process of claim 13 wherein the amount of R'SH employed in the reaction is from about 10% to about 90% of the stoichiometry required to make a 1:1 adduct, resulting in a reaction product comprising a blend of alkylthio- or aryl (heteroyl)thio-substituted p-phenylenediamines and unreacted quinone diimine.

15. The process of claim 13 wherein the reaction is in accordance with the following equation:

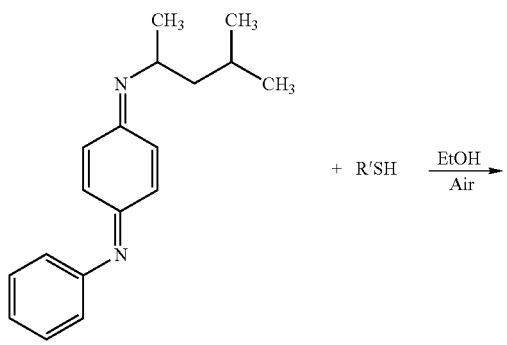

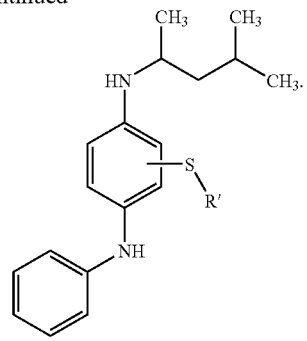

16. The process of claim 13 wherein the reaction conditions comprise stirring the reactants dissolved in an appropriate solvent for at least about 2 hours under a constant stream of air at a temperature of from about 20° C. to about 25° C.

17. The process of claim 16 wherein said solvent comprises ethanol.

18. A rubber composition, the composition comprising natural or synthetic rubber or blend thereof; and one or more phenylenediamine compounds having the formula:

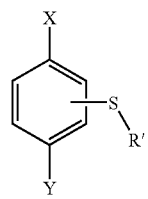

where X and Y are the same or different and selected from $NH_2$ or NHR where R is one selected from the group of alkyl, cycloalkyl, and aryl; and R' is one selected from the group of alkyl, cycloalkyl, aryl, 2-chlorobenzyl, benzyl, 2-carboxyphenyl, mercaptoethyl ether, alkyl 3-propionate, and a heterocyclic moiety, wherein the heterocyclic moiety is one selected from the group consisting of: 2-pyrazines, 3-pyrimidines, 2-pyridines, 3-pyridines, 4-pyridines, 2-pyrimidines, 2-(4,6-dimethyl)pyrimidines, 1,3,5-triazinyl, 2,6-pyridyl, 2,5-thiadiazolyl, 2-toluimidazole, 3-hydroxy-2-mercaptopyridine, and triazenes.

19. The composition of claim 18 wherein the amount of said one or more phenylenediamine compounds in the composition is from 0.5 to about 5.0 phr.

20. The composition of claim 18 comprising a mixture of said one or more of phenylenediamine compounds in combination with a non-thio substituted antidegradant.

21. The composition of claim 20 wherein said non-thio-substituted antidegradant is selected as one from the group consisting of phenylenediamines, dihydroquinolines, phenolics, and a blend thereof.

22. The composition of claim 18 wherein said rubber is one selected from the group of polyisoprene, styrene-butadiene rubber and polybutadiene rubber.

23. The composition of claim 18 comprising from about 0.1 phr to about 5 phr of sulfur, about 0.5 phr to about 2 phr of a vulcanization accelerator, about 0.1 phr to about 5 phr of said one or more phenylenediamine compounds and about 0.1 to about 5 phr of a $C_{12}$-$C_{20}$ fatty acid.

24. The composition of claim 23 wherein said accelerator is a sulfenamide.

25. The composition of claim 23 comprising from about 2 phr to about 3 phr of said one or more phenylenediamine compounds.

26. The composition of claim 1, where Y is NHR with R being an aryl moiety.

27. The composition of claim 26, wherein —SR' is one selected from the group consisting of methyl-3-mercaptopropionate, cyclohexyl mercaptan, dodecyl mercaptan, isopropyl mercaptan, n-butyl mercaptan, t-butyl mercaptan, benzyl mercaptan, 2-chlorobenzyl mercaptan, 1,5-dimercaptoethyl ether, 2-mercaptopyrimidine, 4,6-dimethyl-2-mercaptopyrimidine, 2-mercaptotoluimidazole, phenyl mercaptan, 2-carboxylphenyl mercaptan, and 3-hydroxy-2-mercaptopyridine.

28. The composition of claim 26, wherein X and Y are different.

29. The composition of claim 26, wherein R is phenyl in Y.

30. The composition of claim 29, wherein X is NHR with R being alkyl.

31. The composition of claim 30, wherein R is 1,3-dimethylbutyl.

32. The composition of claim 18, where X and Y are the same or different and each comprise $NH_2$ or NHR, R is alkyl for at least one of X or Y and R' is alkyl.

33. The article of manufacture of claim 12, wherein —SR' is one selected from the group of benzyl mercaptan, 2-chlorobenzyl mercaptan, 1,5-dimercaptoethyl ether, 2-carboxylphenyl mercaptan, and 3-hydroxy-2-mercaptopyridine.

34. A tire comprising a compound having the formula:

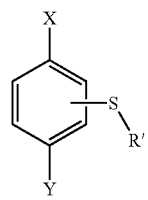

where:
X and Y each comprise NHR where R is one selected from the group of alkyl, cycloalkyl or aryl when X and Y are the same; and R is one selected from the group of hydrogen, alkyl, cycloalkyl or aryl when X and Y are different; and R' is one selected from the group of alkyl, cycloalkyl, aryl, 2-chlorobenzyl, benzyl, 2-carboxyphenyl, mercaptoethylether, alkyl 3-propionate, and a heterocyclic moiety,
wherein the heterocyclic moiety is one selected from the group consisting of: 2-pyrazines, 3-pyrimidines, 2-pyridines, 3-pyridines, 4-pyridines, 2-pyrimidines, 2-(4,6-dimethyl)pyrimidines, 1,3,5-triazinyl, 2,6-pyridyl, 2,5-thiadiazolyl, 2-toluimidazole, 3-hydroxy-2-mercaptopyridine, and triazenes.

35. The tire of claim 34, where at least one of X and Y is NHR, where R is one or more moieties selected from the group consisting of a cycloalkyl and an aryl.

36. The tire of claim 34, where R' is cycloalkyl, aryl, alkyl 3-propionate, 1,3,5-triazinyl, 2,5-thiadiazolyl, or 2,6-pyridyl.

37. The composition of claim 1, where X and Y are NHR with R being cycloalkyl or aryl for at least one of X and Y.

* * * * *